(12) United States Patent
Qi et al.

(10) Patent No.: US 11,512,117 B1
(45) Date of Patent: Nov. 29, 2022

(54) WHOLE AVIAN-ORIGIN REVERSE GENETIC SYSTEM AND RECOMBINANT H5N2 SUBTYPE AVIAN INFLUENZA VIRUS, VACCINE AND USES THEREOF

(71) Applicant: SOUTH CHINA AGRICULTURAL UNIVERSITY, Guangdong (CN)

(72) Inventors: Wenbao Qi, Guangdong (CN); Ming Liao, Guangdong (CN); Yiqun Chen, Guangdong (CN); Jiahao Zhang, Guangdong (CN); Bo Li, Guangdong (CN); Jinyu Huang, Guangdong (CN); Huanan Li, Guangdong (CN)

(73) Assignee: SOUTH CHINA AGRICULTURAL UNIVERSITY, Guangdong (CN)

( * ) Notice: Subject to any disclaimer, the term of this patent is extended or adjusted under 35 U.S.C. 154(b) by 0 days.

(21) Appl. No.: 17/726,567

(22) Filed: Apr. 22, 2022

(30) Foreign Application Priority Data

May 24, 2021 (CN) .......................... 202110564078.6

(51) Int. Cl.
| | |
|---|---|
| *A61K 39/00* | (2006.01) |
| *A61K 39/145* | (2006.01) |
| *A61K 39/12* | (2006.01) |
| *C12N 7/00* | (2006.01) |
| *C07K 14/005* | (2006.01) |

(52) U.S. Cl.
CPC .............. *C07K 14/005* (2013.01); *C12N 7/00* (2013.01); *A61K 39/00* (2013.01); *C12N 2760/16121* (2013.01); *C12N 2760/16122* (2013.01); *C12N 2760/16134* (2013.01); *C12N 2760/16152* (2013.01)

(58) Field of Classification Search
CPC .......... A61P 31/16; C12N 2760/16134; A61K 39/145; A61K 39/12; C07K 14/005
See application file for complete search history.

(56) References Cited

U.S. PATENT DOCUMENTS

2019/0350990 A1   11/2019   Guo et al.

FOREIGN PATENT DOCUMENTS

| CN | 105368833 A | 3/2016 |
|---|---|---|
| CN | 108251557 A | 7/2018 |
| CN | 108642021 A | 10/2018 |
| CN | 109593892 A | 4/2019 |
| WO | 2016192670 A1 | 12/2016 |
| WO | 2018157454 A1 | 9/2018 |

OTHER PUBLICATIONS

Zhang, Xu, Sequence Analysisof H5N6 Subtype AIV and Construction of Vaccine Candidate, College of Veterinary Medicine, South China Agricultural University.
Yang, Lei, et al., Genesis and Dissemination of Highly Pathogenic H5N6 Avian Influenza Viruses, J. Virol., vol. 91, No. 5, Mar. 1, 2017.
Xue, Suqiang, et al., Inactivated Avian Influenza Vaccine for Waterfowl (H5N2 Subtype, D7 Strain), Northern Animal Husbandry, Issue 15, Aug. 5, 2013.
Liao, Ming, H5 subtype avian influenza virus is currently circulating in China, and the construction of its recombinant Vaccine should achieve full coverage in terms of antigenicity. Northern Animal Husbandry, Issue 9, May 5, 2017.
Erich Hoffmann et al., Eight-plasmid system for rapid generation of influenza virus vaccines. Vaccine 20 (2002) 3165-3170.
E. Hoffmann et al., Universal primer set for the full-length amplification of all influenza A viruses, Arch Virol (2001) 146: 2275-2289.

*Primary Examiner* — Barry A Chestnut
(74) *Attorney, Agent, or Firm* — Yue (Robert) Xu; Apex Attorneys at Law, LLP (57) ABSTRACT

The present disclosure discloses a whole avian-origin reverse genetic system, a recombinant H5N2 subtype avian influenza virus, a vaccine containing the virus, and a preparation method and application thereof. The genome of the recombinant virus is comprised of a modified HA gene derived from a highly pathogenic H5N6 subtype avian influenza virus strain, as well as PB2, PB1, PA, NP, NA, M and NS genes derived from H5N2 subtype avian influenza D7 virus strain. The recombinant virus is a recombinant H5N2 avian influenza virus rescued from the D7 virus strain as a backbone, which is an avirulent virus strain with the original immunogenicity, and can maintain a high virus titer during the chick embryo culture process. The recombinant virus fully meets the biological safety requirements and has a good application prospect.

8 Claims, 4 Drawing Sheets

Specification includes a Sequence Listing.

```
            CCTCTAAGAGAAAGAAGAAGGAAAAGAGGACTGTTT    SEQ ID NO: 16
GD123-HA     P  L  R  E  R  K  R  K  R  G  L  F     SEQ ID NO: 15

CCTCTAAGAGAAAGA--------------GGACTGTTT    SEQ ID NO: 18
GD123-rHA    P  L  R  E  R              G  L  F     SEQ ID NO: 17
```

FIG. 5

WHOLE AVIAN-ORIGIN REVERSE GENETIC SYSTEM AND RECOMBINANT H5N2 SUBTYPE AVIAN INFLUENZA VIRUS, VACCINE AND USES THEREOF

CROSS REFERENCE TO RELATED APPLICATIONS

This application claims the priority of Chinese Patent Application No. 202110564078.6, filed on May 24, 2021, and the disclosure of which is hereby incorporated by reference.

FIELD

The present disclosure relates to the technical field of reverse genetics technology and animal vaccines, and specifically relates to a whole avian-origin recombinant H5N2 subtype avian influenza virus, a vaccine, a preparation method and uses thereof.

BACKGROUND

Avian influenza (AI) is an infection and/or disease syndrome caused by avian influenza virus (MV), which seriously affects the development of poultry farming and threatens human health. Poultry can show different clinical symptoms after infection. According to the pathogenicity of the virus, it can be divided into low pathogenic avian influenza (LPAI) virus and highly pathogenic avian influenza (HPAI) virus. Since 2003, avian influenza caused by the highly pathogenic H5 subtype virus has been circulating and even outbreaks in China and other regions of the world. Since 2016, the number of avian influenza outbreaks caused by the highly pathogenic H5 virus has increased significantly in China, and the H5N6 subtype has become the dominant virus affecting Chinese poultry industry. So far, WHO has reported a total of 24 laboratory-confirmed human cases of influenza A (H5N6) infection in China (https://apps.who.int/iris/handle/10665/330697). Therefore, the prevention and control of H5 subtype avian influenza virus is of great significance to the development of poultry industry and public health security.

Inactivated vaccine is one of the effective measures to control H5 subtype avian influenza in China. The HA protein in inactivated avian influenza vaccine plays a decisive role in the immune effect. However, under the pressure of vaccines, drugs and the virus itself, the HA gene of H5 subtype avian influenza virus evolves very fast, and existing vaccines have been unable to effectively prevent and control new variants of H5 subtype avian influenza virus. In the face of the continuous evolution of avian influenza virus, vaccines against H5 subtype avian influenza need to be updated in time to meet the prevention and control of the currently circulating H5 subtype avian influenza virus. In order to meet the needs of rapid and large-scale production of inactivated vaccines, the following conditions must be met: 1. Screening suitable H5 subtype avian influenza virus strains to prepare vaccines; 2. The virus used for vaccines needs to maintain low pathogenicity or even no pathogenicity while maintain the original immunogenicity; 3. The virus can maintain a high virus titer when cultured in chick embryos.

At present, the use of reverse genetics technology to construct avian influenza virus is a commonly used technical mean. This technique rescues the virus strain required for vaccine production by modifying the virus gene in vitro, and thus meets the needs of rapid and large-scale production of inactivated vaccines. In human influenza vaccines, recombinant avian influenza vaccines are constructed by utilizing human influenza virus as a backbone (e.g., Hoffmann E, Krauss S, Perez D et al. Eight-plasmid system for rapid generation of influenza virus vaccines. *Vaccine*, 2002, 20:3165-3170). However, since it contains human genes, it may potentially cause the risk of recombinant avian influenza virus infecting humans, and its safety cannot be guaranteed. Therefore, it is an urgent need to develop a virus strain that is non-pathogenic but maintains the immunogenicity of the virus and can maintain a high virus titer during the chick embryo culture process for the production of a new H5 subtype avian influenza vaccine.

SUMMARY

The first object of the present disclosure is to overcome the above-mentioned shortcomings and deficiencies existing in the prior art, and to provide a whole avian-origin recombinant H5N2 subtype avian influenza virus.

The second object of the present disclosure is to provide a preparation method of the whole avian-origin recombinant H5N2 subtype avian influenza virus.

The third object of the present disclosure is to provide uses of the whole avian-origin recombinant H5N2 subtype avian influenza virus, for example, in the manufacture of a H5N2 subtype avian influenza vaccine which is used to prevent H5N6 subtype avian influenza.

The above-mentioned objects of the present disclosure is achieved by the following technical solutions.

A recombinant H5N2 subtype avian influenza virus, wherein the genome of the recombinant virus is comprised of a modified HA gene derived from a highly pathogenic H5N6 subtype avian influenza virus strain, as well as PB2, PB1, PA, NP, NA, M and NS genes derived from H5N2 subtype avian influenza D7 virus strain; the modified HA gene has a sequence as shown in SEQ ID NO: 9; and the PB2, PB1, PA, NP, NA, M and NS genes derived from D7 strain have nucleotide sequences as shown in SEQ ID NOs: 1-3 and 5-8, respectively.

In the present disclosure, by modifying the segment of HA gene corresponding to the cleavage site of the HA protein from a highly pathogenic H5N6 subtype avian influenza virus (modified from PLRERRRKRGLF (SEQ ID NO: 15) to PLRERGLF (SEQ ID NO: 17)), the virus expressing the modified HA protein has reduced pathogenicity. In addition, through reverse genetics technique, the cleavage site-modified HA gene is recombined with the seven genes from the H5N2 subtype D7 strain in the form of "7+1" to successfully rescue a recombinant H5N2 subtype avian influenza virus. The H5N2 subtype avian influenza D7 virus strain is a virus developed by South China Agricultural University in 2013, and the vaccine prepared with this virus strain is the world's first whole avian-origin H5N2 subtype avian influenza inactivated vaccine for waterfowl. In the present disclosure, the avian influenza D7 virus strain, which is specially used for waterfowl and is highly adapted to chick embryos, is used as the backbone, and all the gene fragments of the rescued recombinant avian influenza virus are derived from avian influenza virus. This preserves the inherent interspecies barrier between the avian influenza virus and the human influenza virus, reduces the risk of the recombinant avian influenza virus infecting humans, and fully meets the biosafety requirements. Besides, the recombinant virus maintains the original immunogenicity and a high virus titer during the chick embryo culture.

The seven genes of the D7 strain, PB2, PB1, PA, NP, NA, M and NS genes, encode the PB2 protein, PB1 protein, PA protein, NP protein, NA protein, M1 protein (encoded by M gene), M2 protein (encoded by M gene), NS1 protein (encoded by NS gene), and NS2/NEP protein (encoded by NS gene) of the virus. Except for the NA protein, the rest are internal proteins of the virus, which are required for the formation of virus particles. HA protein and NA protein are virus surface glycoproteins, among which HA protein is the main protein that determines the antigenicity of influenza virus.

Preferably, the highly pathogenic H5N6 subtype avian influenza virus strain is A/Duck/Guangdong/19123/2019 (H5N6, named according to the World Health Organization standard), abbreviated as GD123 strain.

The present disclosure also provides a preparation method of the recombinant H5N2 subtype avian influenza virus, comprising recombining a modified HA gene derived from a highly pathogenic H5N6 subtype avian influenza virus strain and PB2, PB1, PA, NP, NA, M and NS genes derived from H5N2 subtype avian influenza D7 virus strain to obtain the recombinant virus.

Specifically, the method comprises:

constructing plasmids containing PB2, PB1, PA, NP, NA, M and NS genes derived from H5N2 subtype avian influenza D7 virus strain, respectively; and the plasmids express PB2, PB1, PA, NP, NA, M1 and M2, NS1 and NS2/NEP protein, respectively;

constructing a plasmid expressing the modified HA protein encoded by SEQ ID NO: 9; and mixing the above 8 plasmids, mixing the mixed plasmids with a transfection reagent, and then adding to 293T cells to obtain the recombinant H5N2 subtype avian influenza virus.

Further, the method specifically comprises steps of:

S1. constructing a reverse genetic system comprising 8 plasmids based on H5N2 subtype avian influenza D7 virus strain, the 8 plasmids respectively express proteins encoded by PB2, PB1, PA, HA, NP, NA, M and NS genes derived from H5N2 subtype avian influenza D7 virus strain, and the PB2, PB1, PA, HA, NP, NA, M and NS genes have nucleotide sequences as shown in SEQ ID NOs: 1-8, respectively;

S2. constructing a plasmid expressing the modified HA protein encoded by SEQ ID NO: 9; and S3. mixing 7 plasmids containing PB2, PB1, PA, NP, NA, M and NS genes derived from H5N2 subtype avian influenza D7 virus strain in step S1 with the plasmid expressing the modified HA protein in step S2, mixing the mixed plasmids with a transfection reagent and adding to 293T cells, and culturing the cells to obtain the recombinant H5N2 subtype avian influenza virus.

Preferably, a vector used for constructing the plasmid in step S1 is pSMC vector, and the 8 plasmids obtain by construction are named pSMC-PB2, pSMC-PB1, pSMC-PA, pSMC-HA, pSMC-NP, pSMC-NA, pSMC-M and pSMC-NS, respectively.

Specifically, the pSMC vector is constructed by:

removing BsmBI restriction enzyme site in pCI vector to obtain pCI-NEW vector;

synthesizing a nucleotide fragment containing transcriptional promoter and terminator sequences;

performing double enzyme digestion on the pCI-NEW vector and the nucleotide fragment containing transcriptional promoter and terminator sequences with XhoI and MluI, followed by ligation and transformation to obtain a recombinant plasmid; and performing enzyme digestion identification and DNA sequencing to obtain a positive plasmid as pSMC vector.

As a preferred embodiment, the present disclosure also provides a preparation method of an H5N2 subtype avian influenza inactivated vaccine, which specifically comprises steps of:

(1) Construction pSMC Vector for Reverse Genetic System

First, removing BsmBI restriction enzyme site in pCI vector (product of Promega) by PCR technique to obtain pCI-NEW vector; then synthesizing a DNA fragment containing transcription promoter (pol I promoter) sequence and terminator sequence by gene synthesis; and finally, performing double enzyme digestion on the pCI-NEW vector and the obtained DNA fragment with XhoI and MluI, followed by ligation, transformation and identification to obtain a positive plasmid as pSMC vector.

(2) Construction and Identification of H5N2 Subtype D7 Reverse Genetic System

Amplifying eight gene fragments (PB2, PB1, PA, HA, NP, NA, M, and NS) derived from the D7 virus strain respectively, and then ligating the fragment to the reverse genetic system vector pSMC, and the obtained positive plasmids are named pSMC-PB2, pSMC-PB1, pSMC-PA, pSMC-HA, pSMC-NP, pSMC-NA, pSMC-M and pSMC-NS respectively, that is to establish a reverse genetic system based on the D7 strain as an avian influenza vaccine development platform. Co-transfecting the above 8 plasmids into 293T cells, and 48 h later, inoculating the cell culture supernatant into 9~11-day-old SPF (specific-pathogen-free) chick embryos, and collecting the virus. After testing, the successfully rescued virus can be stably passaged in chick embryos. After sequencing identification, the reverse genetic system is successfully constructed.

(3) Amplification of HA Gene Fragment for Recombinant Virus

Designing overlap primers based on the sequence of HA gene derived from the highly pathogenic H5N6 subtype avian influenza GD123 virus strain in order to delete the cleavage site of the HA gene. Site-directly modifying the sequence of HA gene by the overlap extension PCR and fusion PCR method, and the modified fragment is named rHA. The rHA gene has a sequence as shown in SEQ ID NO: 9.

(4) Construction of the Target Plasmid

Performing enzyme digestion with restriction endonuclease BsmBI followed by ligation to insert the rHA fragment into the pSMC expression vector, and the positive recombinant plasmid identified by sequencing is named pSMC-rHA.

(5) Rescue of Recombinant Virus rGD123

Co-transfecting the recombinant plasmid pSMC-rHA with pSMC-PB2, pSMC-PB1, pSMC-PA, pSMC-NP, pSMC-NA, pSMC-M and pSMC-NS of the D7 reverse genetic system into 293T cells. After 48 h, the transfected cells and supernatant is collected and inoculated into 9~11-day-old SPF chick embryos. After 60 h, detecting the hemagglutination activity, and harvesting the allantoic fluid with hemagglutination activity. After identification by PCR and sequencing, the obtained virus is the target recombinant virus, named rGD123, a new recombinant H5N2 subtype avian influenza virus.

The present disclosure also provides an H5N2 subtype avian influenza vaccine H51901, comprising an immunizing amount of the above-mentioned recombinant H5N2 subtype avian influenza virus rGD123 as an antigen. The vaccine has excellent antigen matching and safety, can induce poultry to produce high-level antibodies, and shows good protection effect, which provides an effective tool for the prevention and control of avian influenza.

The present disclosure also provides use of the above-mentioned recombinant H5N2 subtype avian influenza virus rGD123 or vaccine H51901 in the manufacture of a medicament for preventing and/or treating H5 subtype avian influenza. The H5 subtype avian influenza is mainly include the H5N6 subtype avian influenza that has been widely prevalent in recent years, but is not limited to the H5N6 subtype avian influenza.

Compared with the prior art, the present disclosure has the following beneficial effects.

The present disclosure provides whole avian-origin H5N2 subtype avian influenza virus strain. The recombinant virus is rescued by constructing the H5N2 subtype avian influenza D7 reverse genetic system and combining with the modified HA gene derived from the highly pathogenic H5N6 subtype avian influenza virus strain in the form of "7+1". The recombinant virus can maintain high growth titer and good antigenicity in chick embryos. In addition, the virus is a recombinant virus constructed with the D7 virus strain as the backbone, which is a non-pathogenic strain, so that the recombinant virus fully meets the biological safety requirements. The vaccine H51901 with excellent antigen matching and safety, which is developed based on the recombinant virus can induce poultry to produce high levels of antibodies and show good protective effects, which provides an effective tool for the prevention and control of avian influenza.

DETAILED DESCRIPTION

The present disclosure is further described below in conjunction with the accompanying drawings and specific examples. However, the examples do not limit the present disclosure in any form. Unless otherwise specified, the reagents, methods and equipment used in the present disclosure are conventional reagents, methods and equipment in the technical field.

Unless otherwise specified, the reagents and materials used in the following examples are commercially available.

Polynucleotides encoding viral proteins can be synthesized artificially according to the sequences disclosed in the present invention, and commonly used promoters, transcription terminators, resistance genes, etc. can be synthesized according to the prior art.

The avian influenza virus strain A/Duck/Guangdong/D7/2007 (H5N2, referred to as the D7 strain or D7 virus strain) is isolated and preserved by the National and Regional Joint Engineering Laboratory for Medicament of Zoonoses Prevention and Control.

The highly pathogenic avian influenza strain A/Duck/Guangdong/19123/2019 (H5N6, referred to as GD123 strain or GD123 virus strain) was isolated and preserved by the National and Regional Joint Engineering Laboratory for Medicament of Zoonoses Prevention and Control.

Figure 1:
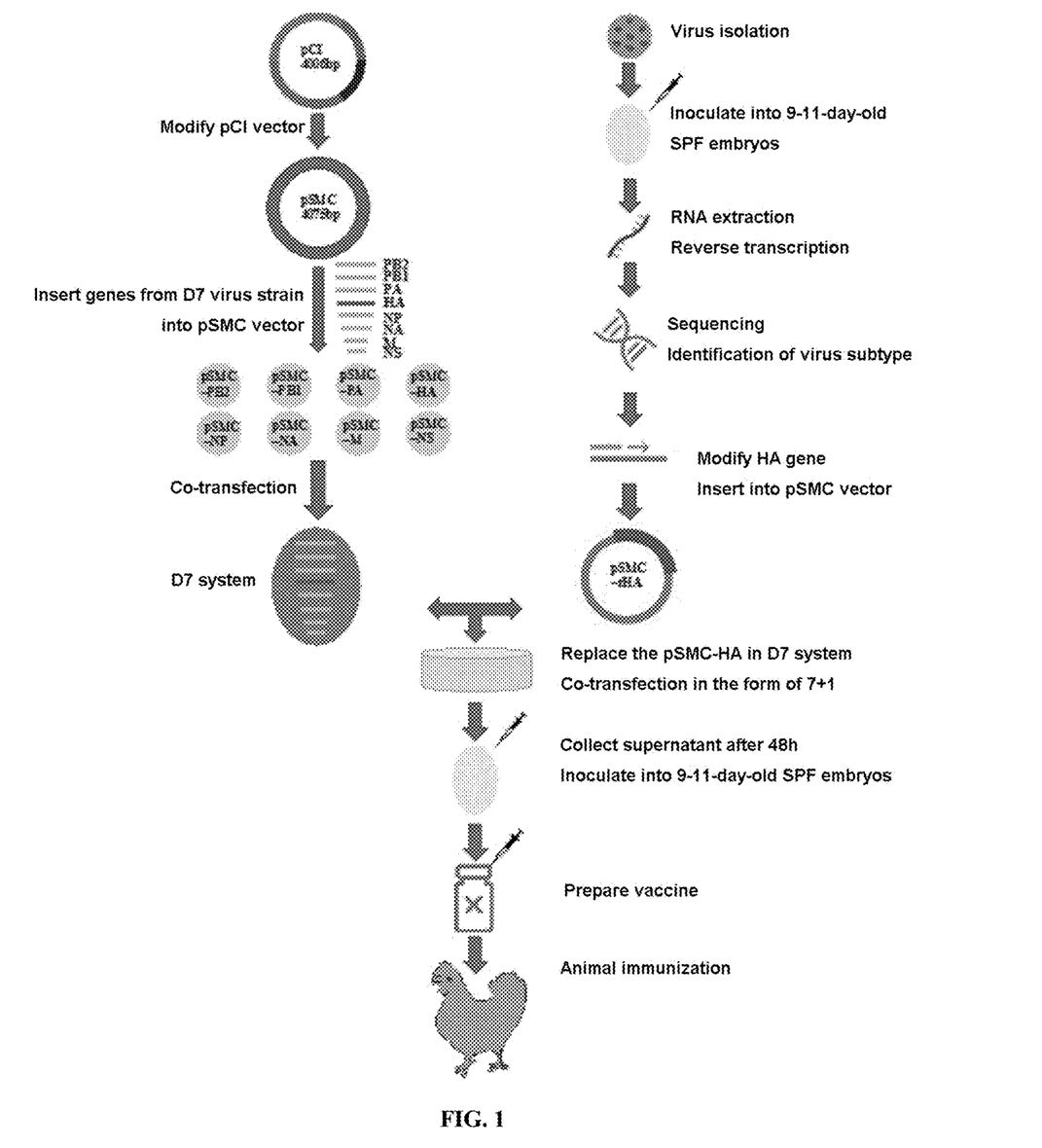
FIG. 1 is the construction flow chart and use of avian influenza vaccine H51901 in the present disclosure.

The construction flow chart and uses of the avian influenza vaccine H51901 of the present disclosure are shown in FIG. 1, which specifically includes the following embodiments.

Deposit information: The recombinant H5N2 subtype avian influenza virus rGD123 was deposited under a deposit accession number of CCTCC NO: V202218 in the China Center for Type Culture Collection (Address: No. 299, Bayi Road, Wuchang District, Wuhan City, Hubei Province, China) on Mar. 8, 2022.

Figure 2:
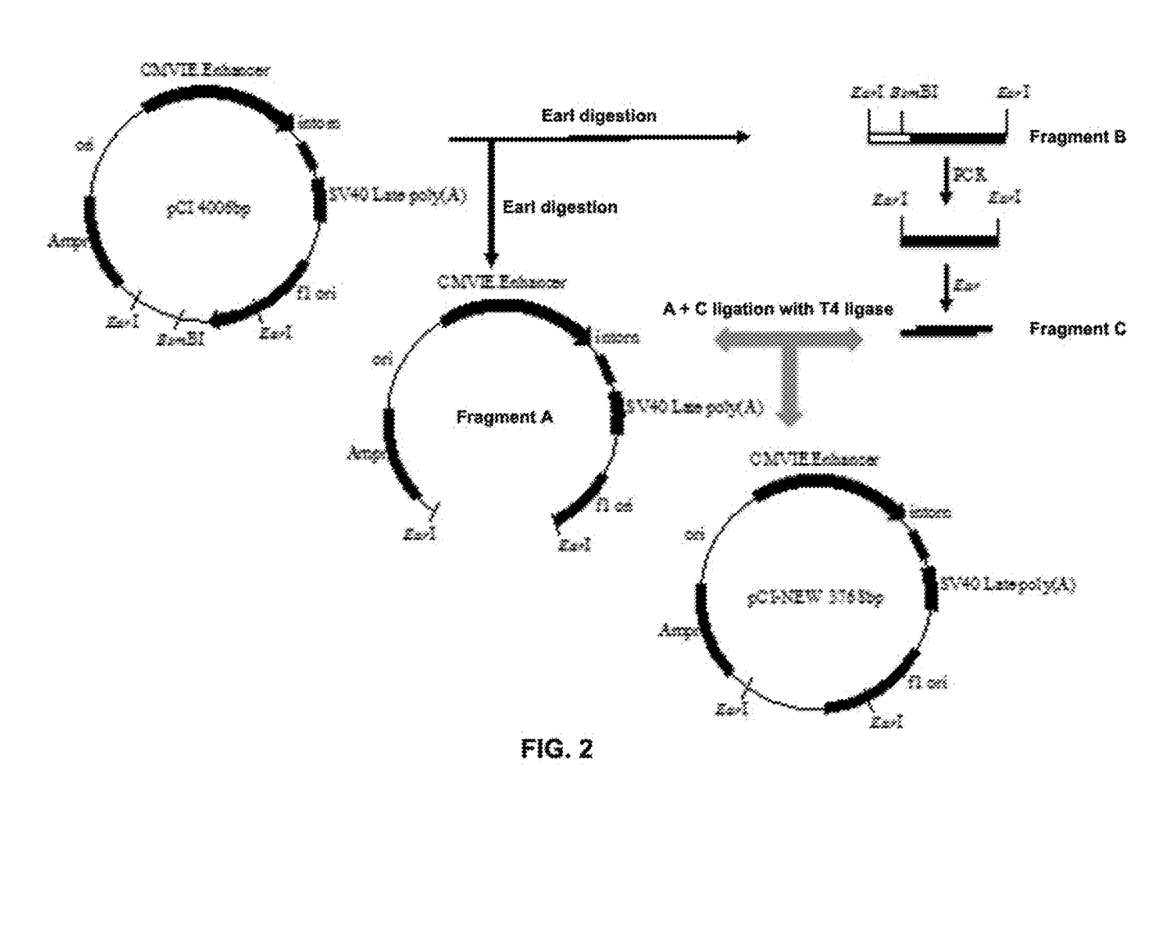
FIG. 2 is a schematic diagram of the construction of the pCI-NEW vector in the present disclosure.
Figure 3:
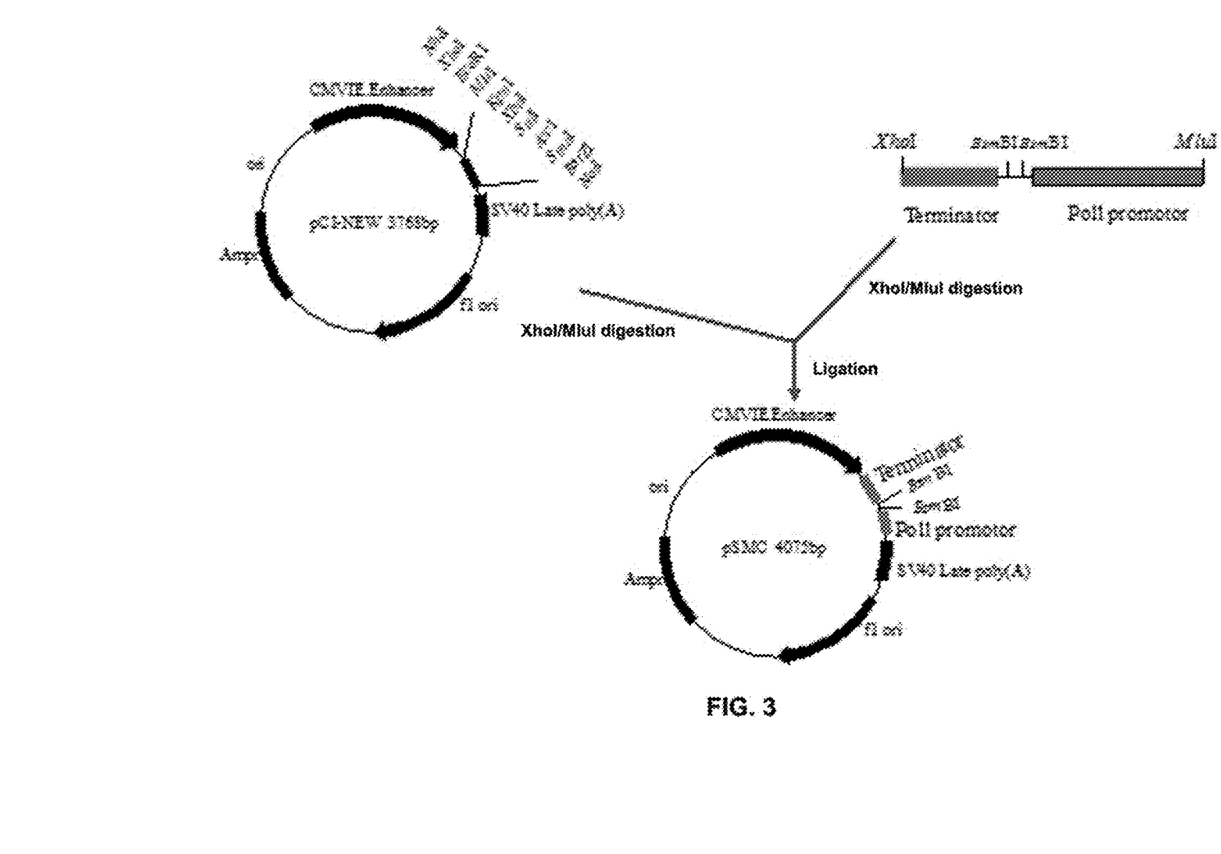
FIG. 3 is a schematic diagram of the construction of pSMC vector in the present disclosure.

Example 1 Construction of a Whole Avian-Origin Reverse Genetic System Based on D7 Strain for Avian Influenza Vaccine 1. Construction of the Reverse Genetic System Vector pSMC (FIG. 2 and FIG. 3)

(1) Engineering of pCI Vector

The pCI vector was a product of Promega (Cat. No. BR180). In order to remove the BsmBI restriction enzyme site in the pCI vector, the pCI vector was digested with the restriction endonuclease EarI to obtain a long fragment A and a short fragment B. The amplification primers pCI-EarI-1 and pCI-EarI-2 were designed according to the sequence of short fragment B.

pCI-EarI-1: 5'-TAGCGAGAGGCCGCACG-3' (SEQ ID NO: 10);

pCI-EarI-2: 5'-TCTTCGTTCGGTCACAGCTTCTGTAAG-3' (SEQ ID NO: 11).

PCR amplification was carried out using short fragment B as a template to obtain fragment C, which was recovered. Fragment C and fragment A were digested and recovered with EarI respectively, and then ligated. After transformation and plasmid extraction, enzyme digestion with BsmBI and identification by sequencing was performed, and the plasmid verified to be correct was named as pCI-NEW vector.

(2) Acquisition of Transcription Elements

DNA fragments containing transcription elements (pol I promoter and common transcription terminator) were obtained by gene synthesis. The sequence of the terminator is CCAGGGTACTGGTCCTGACCACGTTGGAGGGGGGA (SEQ ID NO: 12).

(3) Enzyme Digestion of pCI-NEW Vector and Transcription Element Fragments

The pCI-NEW vector and the DNA fragment synthesized in step (2) were subjected to double digestion with XhoI and MluI.

(4) Ligation and Transformation of Digestion Products from pCI-NEW Vector and Transcription Element Fragments The digestion products from the pCI-NEW vector and transcription element fragments in step (3) were recovered, and subjected to ligation, transformation, plasmid extraction, and enzyme digestion identification.

(5) Enzyme Digestion Identification

The plasmids extracted in step (4) were identified by single digestion with BsmBI and double digestion with XhoI and MluI, respectively.

(6) Sequencing Identification

The plasmids identified as positive by enzyme digestion in step (5) were sequenced, and the plasmid whose sequence was verified to be correct was named pSMC vector.

2. Construction of D7 Reverse Genetics System

Eight gene fragments of D7 strain (PB2, PB1, PA, HA, NP, NA, M and NS genes) were amplified with reference to universal primers of 8 gene sequences of influenza virus (Universal primer set for the full-length amplification of all influenza A viruses. Arch Virol. 2001 December; 146 (12): 2275-89). The 8 gene fragments derived from the D7 virus strain obtained by amplification were inserted into the reverse genetic vector pSMC according to the conventional molecular biology operation method, and the obtained 8 plasmids were named pSMC-PB2, pSMC-PB1, pSMC-PA, pSMC-HA, pSMC-NP, pSMC-NA, pSMC-M and pSMC-NS. A D7 reverse genetic system vaccine development platform was established to provide the required genes for vaccine strains. After 8 plasmids were co-transfected into 293T cells, the H5N2 avian influenza virus with hemagglutination activity could be successfully assembled, and could be stably passaged on chick embryos. After sequencing identification, it was proved that the reverse genetic system was successfully constructed.

Example 2 Construction of Recombinant H5N2 Subtype Avian Influenza Virus

1. Extraction and Reverse Transcription of Viral RNA

Total RNA from virus-containing allantoic fluid was extracted using a total RNA extraction kit. cDNA was obtained by reverse transcription according to the instructions of M-MLV reverse transcriptase.

2. Design of Segmented Primers

Overlap primers (SEQ ID NO: 13 and SEQ ID NO: 14) for modifying the cleavage site of the HA gene were designed based on the HA sequence of the GD123 strain. The specific sequence is as follows.

GD123-HA1-F:
5'-CTCAGAAATAGTCCTCTAAGAGAAAGAGGACT GTTTGGAGCT-3' (SEQ ID NO: 13);

GD123-HA2-R:
5'-AAACAGTCCTCTTTCTCTTAGAGGACTATTTCT- GAGCC-3' (SEQ ID NO: 14).

3. Modification, Amplification and Purification of HA Fragment

Fragmented PCR amplification and fusion PCR amplification of the HA gene of GD123 strain were carried out using high-fidelity DNA polymerase and fragmented primers.

Figure 4:
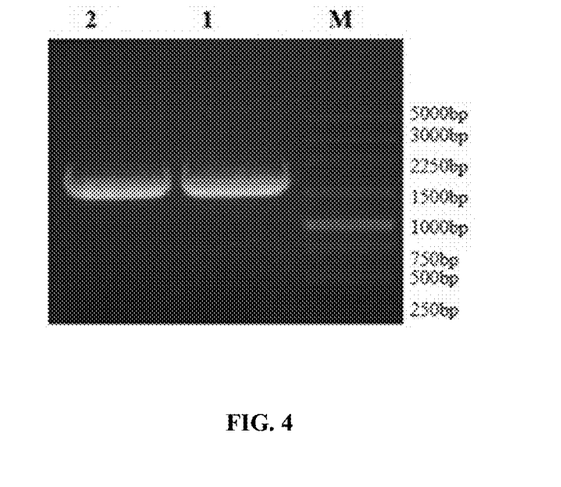
FIG. 4 is the results of PCR amplification of the HA gene of the donor virus strain and the modified HA gene in the present disclosure. Lane 1 is the modified HA gene, lane 2 is the HA gene of the donor virus strain; M is the 250 bp DNA Ladder.
Figure 5:
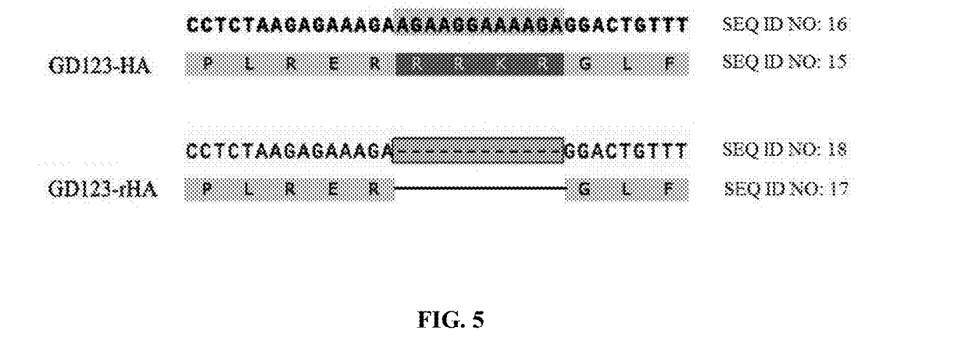
FIG. 5 is a comparison diagram of the modified rHA gene cleavage site sequence and the original sequence in the present disclosure.

The upstream and downstream universal primers with BsmBI restriction sites were paired with segmented primers, respectively, and two fragments, HA1 and HA2, were amplified. Finally, fusion PCR was performed to amplify the complete modified HA fragment. After PCR amplification, the amplified products were preliminarily detected by 1% agarose gel electrophoresis (the amplification results are shown in FIG. 4), and the modified HA gene fragments were recovered and named rHA. The rHA was identified by sequencing and compared with the original sequence, and it was confirmed that the cleavage site had been successfully modified (as shown in FIG. 5). The rHA gene sequence is shown in SEQ ID NO: 9.

4. Construction, Screening and Purification of the Target Plasmid

The amplified target fragment rHA and pSMC expression vector were digested with restriction endonuclease BsmBI (55° C. water bath for 3 h).

The digested products were recovered, ligated and transformed into DH5a competent cells, which were cultured at 37° C. overnight, and the positive clones were initially screened by PCR (bacteria suspension as template). The specific operation is as follows: a single colony was picked out and transferred into an EP tube containing 500 μL of LB medium (ampicillin-resistant), which was then placed on a shaker at 37° C. and cultured with shaking for 3-4 h. 2 μL of bacterial suspension was used for PCR amplification, and 10 μL of PCR product was subjected to electrophoresis detection. The PCR-positive clones were identified by sequencing. The clones with correct sequencing were further expanded and cultured, and the plasmids were extracted. The concentration and purity of the plasmids were determined, and stored at −40° C. for future use.

5. Rescue and Identification of Recombinant Virus rGD123

Cell preparation. One day before transfection, 293T cells were digested with trypsin and counted. Cells of appropriate concentration were added to a 12-well cell culture plate, which was then placed in a 37° C. incubator containing 5% $CO_2$. The cells were used for experiments when the cell density reached about 90%.

Transfection

Eight plasmids (300 ng/plasmid) required for transfection were added into EP tubes containing 150 μL serum-free medium Opti-MEM, mixed well, and named as solution A; 4.8 μL Lipofectamine 2000 (Invitrogen) was added to another EP tube containing 150 μL of Opti-MEM, named solution B, mixed well, and allowed to stand at room temperature for 5 min. Solution A was added to solution B, mixed gently and allowed to stand for 20 min. The 12-well culture plate with 293T cells was taken out, and the original medium was discarded. The plate was then washed twice with sterilized PBS, the mixture of plasmid and liposome was added, and the plate was placed in a 37° C. incubator with 5% $CO_2$ for 4-6 h of culture. Then the DMEM medium containing BSA (concentration of 0.2%) was used to replace the medium containing Lipofectamine 2000 to continue the culture. After 48 h, the supernatant and cells were collected, mixed well and inoculated to 9~11-day-old SPF embryos. After 60 h of inoculation, the allantoic fluid was tested for hemagglutination activity. The presence of hemagglutination activity indicated that it contained influenza virus. Allantoic fluid with hemagglutination activity was harvested and sequenced to identify the virus sequence. The virus was continuously passaged for five generations, and after collection, it was aliquoted and stored at −80° C. for future use.

Identification of the Recombinant Virus

The RNA of the successfully rescued virus was extracted and subjected to whole genome sequencing by RT-PCR. After verification, the obtained recombinant virus was named rGD123.

Example 3 Preparation of Vaccine H51901 with Recombinant Virus rGD123

1. Preparation of Vaccine

Large-scale preparation of antigens. The rGD123 virus used for vaccine preparation was diluted to about $1\times10^{-4}$ $TCID_{50}$/mL using sterile DMEM cell culture medium, and the diluted virus was inoculated to allantoic cavity of 9~11-day-old SPF chick embryos at 0.2 mL/embryo under sterile conditions, sealed and placed in a 37° C. incubator. After 60 h of incubation, chick embryo allantoic fluid was collected in a biological safety cabin, and the hemagglutination (HA) titer was determined.

Antigen Inactivation

The virus collected above was inactivated with a final concentration of 0.1% formaldehyde, sealed, placed in a shaker, and incubated at 37° C. for 24 h; then the inactivated virus was inoculated to 9~11-day-old SPF chick embryos at 0.2 mL/embryo. After culture at 37° C. for 48 h, the hemagglutination titer was tested to verify whether the virus had been completely inactivated.

Preparation of Inactivated Oil Emulsion Vaccine H51901

Preparation of water phase: 97 parts of the solution containing the inactivated rGD123 virus and 3 parts of Tween-80 were mixed well. Preparation of oil phase: 94 parts of Marcol-52 white mineral oil and 6 parts of Span-80 were mixed well and sterilized by autoclaving for future use. The oil phase and the water phase in a ratio of 2:1 were emulsified using an emulsifier at 25,000 r/min for 5 min. During the emulsification, a few drops of the mixture can be placed on the surface of cold water. In the case that only the first drop diffused and the others did not, the formulation is judged to be water-in-oil, and the preparation of the inactivated oil emulsion vaccine was completed. The prepared vaccine was put into a centrifuge to centrifuge at 3,000 r/min for 15 min, and the presence of stratification was observed. If absent, the preparation was successful. The vaccine, named H51901, was aliquoted and stored at 4° C.

2. Immune Challenge Protection Test of H51901 Vaccine Strain in SPF Chicken

In order to verify the immune effect of the H51901 vaccine strain, SPF chickens aged 21-28 days were subcutaneously injected with the recombinant avian influenza inactivated vaccine H51901 through the neck at 0.3 mL/bird as the experimental group; another 5 chickens of the same batch were used as the non-immune blank control group. At 21 dpi (21 days after immunization), they were marked one by one and blood was collected to separate serum for HI (haemagglutination inhibition) antibody test. The H5N6 subtype avian influenza GD123 strain, 19147 strain, 19229 strain, 19245 strain, 19396 strain and 20090 strain were used to challenge the chickens of the experimental group and the control group, and the morbidity or death of the experimental chickens was observed very day and recorded in time for 14 days. At 5 dpc (5 days after the challenge), the throat and cloacal swabs of the experimental chickens were collected for virus isolation, and the protection status was counted.

TABLE 1

Protection of H51901 vaccine against H5N6 subtype avian influenza

| Group | Strain | HI (log2) Mean Antibody Titer | Protection Rate (%) |
|---|---|---|---|
| H51901 Treatment group | GD123 | 10.5 | 100% (10/10) |
| | 19174 | 10.4 | 89% (8/9) |
| | 19229 | 10.5 | 80% (8/10) |
| | 19245 | 10.1 | 80% (8/10) |
| | 19396 | 10.5 | 100% (10/10) |
| | 20090 | 8.6 | 100% (10/10) |
| Control group | | 0 | 0% (0/30) |

The results of the challenge protection test of the recombinant avian influenza inactivated vaccine strain H51901 showed that the vaccine had a good immune effect on SPF chickens aged 21-28 days. After 21 days of immunization, serum from the SPF chicken can cross-react with highly pathogenic avian influenza virus GD123 strain, 19147 strain, 19229 strain, 19245 strain, 19396 strain and 20090 strain of H5N6 subtype, with HI titer ≥8.6 log 2, demonstrating that the vaccine induced high level of antibody in vivo, and produce complete protection against challenge from GD123 strain, 19396 strain and 20090 strain with a protection rate up to 100%. For other H5N6 circulating virus strains, 19174, 19229 or 19245, vaccine H51901 can also induce immunized chickens to produce high level of antibody, and the positive rate of virus isolation from throat and cloacal swabs of test chickens was extremely low, giving a protection rate of 80%-89%. In contrast, antibody was not detectable in SPF control chickens. The results showed that the vaccine H51901 had good immunogenicity, and the antibodies produced in the immunized animal had a good neutralization effect on the H5N6 viruses circulating in the recent two years.

3. Serum Hemagglutination Inhibition Test (HI Test) for Cross-Reactivity

The serum from SPF chickens immunized with H51901 vaccine or the positive serum from chickens infected with donor strain GD123 and some H5N6 subtype virus strains were subjected to serum HI test for cross-reactivity. The test results are shown in Table 2. Both the positive serum produced after immunization with H51901 vaccine and the positive serum after GD123 virus infection can give hemagglutination inhibition with 8 highly pathogenic avian influenza H5N6 virus strains, indicating that the immunogenicity of the circulating highly pathogenic avian influenza H5N6 virus strain was basically consistent with that of GD123 wild-type virus. Therefore, the serum of SPF chickens immunized with H51901 vaccine can produce good serological cross-reaction with the circulating highly pathogenic H5N6 subtype avian influenza strains as well, with HI titer ≥5 log 2. According to the Chinese Veterinary Pharmacopoeia, the HI titer of avian influenza vaccine being ≥4 log 2 shows that the vaccine can induce the body to produce antibodies with protective effect. Therefore, the H51901 vaccine can induce the animal to produce enough antibodies to against the infection of the highly pathogenic H5N6 subtype avian influenza epidemic strains.

TABLE 2

HI (log2) cross-test results

| Antigen | Serum | |
|---|---|---|
| (virus strain) | H51901 | GD123 |
| GD123 | 5 | 8 |
| H51901 | 9 | 10 |
| 19046 | 6 | 8 |
| 19049(2) | 6 | 9 |
| 19051(2) | 6 | 9 |
| 19073(1) | 7 | 9 |
| 19076 | 7 | 9 |
| 19134 | 6 | 9 |
| 19324(2) | 7 | 9 |
| 19374 | 6 | 8 |

In conclusion, H51901 can be used as an ideal inactivated vaccine for the prevention and control of the H5 subtype avian influenza, which is dominated by the H5N6 subtype widespread in recent years.

The above-mentioned embodiments are preferred embodiments of the present disclosure, but the embodiments of the present disclosure are not limited by the above-mentioned embodiments. Any other changes, modifications, substitutions, combinations, and simplifications that do not depart from the spirit and principle of the present disclosure should be equivalent embodiments and are included within the protection scope of the present disclosure.

What is claimed is:

1. A recombinant H5N2 subtype avian influenza virus, wherein the genome of the recombinant virus is comprised of a modified HA gene derived from a highly pathogenic H5N6 subtype avian influenza virus strain, as well as PB2, PB1, PA, NP, NA, M and NS genes derived from H5N2 subtype avian influenza D7 virus strain; the modified HA gene has a sequence as shown in SEQ ID NO: 9; the PB2, PB1, PA, NP, NA, M and NS genes derived from D7 strain have nucleotide sequences as shown in SEQ ID NOs: 1-3 and 5-8, respectively; the H5N6 subtype avian influenza virus strain is A/Duck/Guangdong/19123/2019 (H5N6); and the recombinant virus has a deposit accession number of CCTCC NO: V202218.

2. A preparation method of the recombinant virus according to claim 1, comprising recombining a modified HA gene derived from a highly pathogenic H5N6 subtype avian influenza virus strain and PB2, PB1, PA, NP, NA, M and NS genes derived from H5N2 subtype avian influenza D7 virus strain to obtain the recombinant virus.

3. The preparation method according to claim 2, wherein the method comprises:
  constructing plasmids expressing a protein encoded by PB2, PB1, PA, NP, NA, M and NS genes derived from H5N2 subtype avian influenza D7 virus strain, respectively;
  constructing a plasmid expressing a modified HA protein encoded by SEQ ID NO: 9; and
  mixing the above 8 plasmids, mixing the mixed plasmids with a transfection reagent, and then adding to 293T cells to obtain the recombinant H5N2 subtype avian influenza virus.

4. The preparation method according to claim 2, wherein the method comprises steps of:
  S1. Constructing a reverse genetic system comprising 8 plasmids based on H5N2 subtype avian influenza D7 virus strain, the 8 plasmids respectively contain 8 genes derived from H5N2 subtype avian influenza D7 virus strain, PB2, PB1, PA, HA, NP, NA, M and NS genes, and the 8 genes have nucleotide sequences as shown in SEQ ID NOs: 1-8, respectively;
  S2. constructing a plasmid expressing the modified HA protein encoded by SEQ ID NO: 9; and
  S3. mixing 7 plasmids containing PB2, PB1, PA, NP, NA, M and NS genes derived from H5N2 subtype avian influenza D7 virus strain in step S1 with the plasmid expressing the modified HA protein in step S2, mixing the mixed plasmids with a transfection reagent and adding to 293T cells, and culturing the cells to obtain the recombinant H5N2 subtype avian influenza virus.

5. The preparation method according to claim 4, wherein a vector used for constructing the plasmid in step S1 is pSMC vector, and the 8 plasmids obtain by construction are named pSMC-PB2, pSMC-PB1, pSMC-PA, pSMC-HA, pSMC-NP, pSMC-NA, pSMC-M and pSMC-NS, respectively.

6. The preparation method according to claim 5, wherein the pSMC vector is constructed by:
  removing BsmBI restriction enzyme site in pCI vector to obtain pCI-NEW vector;
  synthesizing a nucleotide fragment containing transcriptional promoter and terminator sequences;
  performing double enzyme digestion on the pCI-NEW vector and the nucleotide fragment containing transcriptional promoter and terminator sequences with XhoI and MluI, followed by ligation and transformation to obtain a recombinant plasmid; and
  performing enzyme digestion identification and DNA sequencing to obtain a positive plasmid as pSMC vector.

7. A recombinant H5N2 subtype avian influenza vaccine based on reverse genetic technique, comprising an immunizing amount of the recombinant H5N2 subtype avian influenza virus according to claim 1 as an antigen.

8. Use of the recombinant H5N2 subtype avian influenza virus according to claim 1 in the manufacture of a vaccine for preventing H5N2 subtype avian influenza.

\* \* \* \* \*

SEQUENCE LISTING

<160> NUMBER OF SEQ ID NOS: 18

<210> SEQ ID NO 1
<211> LENGTH: 2280
<212> TYPE: DNA
<213> ORGANISM: Artificial Sequence
<220> FEATURE:
<223> OTHER INFORMATION: Synthesized PB2 gene nucleotide sequence

<400> SEQUENCE: 1

```
atggagagaa taaaagaatt aagagagcta atgtcgcaat cccgcacctg cgagatacta     60
acaaaaacca ctgtggacca tatggccata attaagaaat acacatcagg aagacaagag    120
aagaaccctg ctctcagaat gaaatggatg atggcaatga aatatccaat caccgcaaac    180
aagagaataa tggagatgat tcctgaaagg aatgaacaag gacagacgct gtggagcaag    240
acaaatgatg ctggatcgga cagggtaatg gtgtctcccc tagccgtaac atggtggaac    300
aggaatgggc cgacaacaag tacagtccat tatccaaaag tttacaaaac atactttgag    360
aaagttgaaa ggttaaaaca tggaacattt ggtcccgttc atttccgaaa ccaagttaaa    420
atacgccgcc gagttgatgt aaacccgggt catgcagatc tcagtgctaa agaagcacaa    480
gatgtcatca tggaggtagt tttcacaaat gaagtgggag ctagaatatt gacatcagaa    540
tcgcaattag caataacaaa agagaagaaa gaagagctcc aggattgtaa gattgctcct    600
ttaatggtgg cttacatgtt ggaaagggaa ctagttcgga aaactaggtt cctaccagta    660
tcaggcggga caagtagtgt gtacattgag gtattgcact tgactcaggg tacctgctgg    720
gaacagatgt acaccccggg cggagaagtg agaaatgatg atgttgacca gagtttgatc    780
attgctgcta gaaacattgt taggagagca acagtatcag ctgatccact gctatcacta    840
ttggagatgt gccacagcac acagatcggt gggataagga tggtggacat tctcaggcaa    900
aatccaactg aggagcaagc tgtggatata tgcaaagcag caatgggtct gagaatcagt    960
tcgtctttta gctttggagg cttcactttc aaaagaacaa gtggatcgtc tgtaaagaaa   1020
gaagaagaag tgcttacagg caacctccaa acattgagga ttagaataca tgaggggtat   1080
gaggagttca caatggttgg acggagggca acagctatcc tgaggaaagc aactagaagg   1140
ctgattcagt tgatagtaag tggaagagat gaacaatcaa ttgctgaagc aattattgta   1200
gcaatggtgt tctcacagga ggagtgtatg ataaaggcag tccgtggcga tttgaatttt   1260
gtaaacagag caaaccaaag attgaacccc atgcatcaac tcctgaggca cttccaaaag   1320
gatgcaaaag tgctatttca gaactgggga attgaaccca ttgacaatgt catggggatg   1380
atcggaatat tacccgatat gactccaagc acagagatgt cactgagagg ggtgagagtt   1440
agtaagatgg gagtggatga atattccagc actgagaggg tgactgtgag cattgaccgt   1500
ttcttaaggg tccgagatca gctggggaac atactactat ctcccgaaga agtgagtgaa   1560
acacaggaaa cagagaaatt gacgataaca tattcatcat caatgatgtg ggaaatcaat   1620
ggtcctgagt cagtacttgt taacacctat caatggatca tcagaaattg ggagaccgtt   1680
aagattcaat ggtctcaaga ccctactatg ttgtacaata aaatggagtt tgaaccgttc   1740
caatccctgg tacccaaagc tgccagaagt ctatacagtg gatttgtgag aacactattc   1800
caacaaatgc gtgatatact gggaacattt gataccgttc aaataataaa gctgctacca   1860
tttgcagcag ccccaccgga gcagagcaga atgcagtttt cttccctaac tgtaaatgtg   1920
agaggctcag gaatgagaat actcgtaagg ggtaactccc ctgtgttcaa ttacaataag   1980
gtaaccaaaa ggcttacagt actcggaaag gatgcagggg cactgacaga agatccagat   2040
```

-continued

```
gagggaacag ccggagtgga gtctgcggta ctaaggggat tcttaattct aggcaaggag 2100
gacagaagat atggaccagc attaagcatc agtgaactga gcaatcttgc gaaaggggag 2160
aaagctaatg tgctgatagg gcaaggagac gtagtgttgg taatgaaacg gaaacgggac 2220
tctagcatac ttactgacag ccagacagcg accaaaagga ttcggatggc catcaattag 2280
```

<210> SEQ ID NO 2
<211> LENGTH: 2274
<212> TYPE: DNA
<213> ORGANISM: Artificial Sequence
<220> FEATURE:
<223> OTHER INFORMATION: Synthesized PB1 gene nucleotide sequence

<400> SEQUENCE: 2

```
atggatgtca atccgactct acttttcttg aaagtgccag tgcaaaatgc tataagtacc 60
acattccctt atactggaga tcctccatac agccatggaa caggaacagg atacaccatg 120
gacacggtca acagaacaca tcaatactca gaaaagggga aatggacaac aaacacagaa 180
actaaagcac cccaactcaa cccgattgac gggccgttgc ctgatgataa tgaaccgagc 240
gggtacgcac aaacggactg cgtgttggaa gcaatggctt tcctggaaga atcacaccca 300
gggattttcg aaaactcgtg tcttgaaaca atggaagttg ttcagcaaac aagagtggat 360
aaactaaccc aaggtcgcca gacctatgac tggacattga atagaaatca gccggctgct 420
actgcattgg ccaacaccat agaggtcttc agatcgaacg gtctaacagc taatgaatca 480
gggaggctaa tagatttcct aaaggacgtg acggactcaa tgaataaaga ggaaatggaa 540
ataacgaaac atttccagag aaagagaaga gtaagggaca acatgaccaa gaaaatggtc 600
acacaaagaa caatagggaa gaagaagcag aggctgaaca ggaggagcta tttaataaga 660
gcactgacac tgaacacaat gacaaaagat gcagaaagag gcaaattgaa aaggagggca 720
attgcaacgc ccggaatgca gatcagagga ttcgtgtact ttgtcgaaac actagcaagg 780
agcatttgtg agaaacttga gcaatctgga ctcccagttg gagggaacga gaagaaggct 840
aaactggcaa acgtcgtgag aaagatgatg actaactcac aagatacaga gctctccttt 900
acaattactg gggacaacac caaatggaat gagaatcaga atcctagagt gtttctagcg 960
atgataacat atattacaag aaatcaacct gaatggttta gaaatgtctt gagtattgct 1020
cctataatgt tctcaaacaa aatggcgaga ttagggaaag ggtacatgtt cgaaagcaag 1080
agcatgaagc tacggacaca agtaccagca gaaatgcttg caaccattga cctgaaatac 1140
ttcaatgaat caacgagaaa gaaaatcgag aaaataagac ctcttctaat agagggcaca 1200
gcctcattga gtcctggaat gatgatgggc atgttcaaca tgctgagtac ggtcttagga 1260
gtttcaatcc tgaatcttgg gcaaaagagg tacaccaaaa ccacatactg gtgggacgga 1320
ctccaatcct ctgatgattt cgccctaata gtgaatgcac caaatcatga gggaatacaa 1380
gctggggtag ataggttcta taggacctgc aaactagttg gaatcaatat gagcaaaaag 1440
aagtcttata taaataggac aggaacattt gagttcacaa gtttttttcta ccgttatgga 1500
tttgtggcca acttcagtat ggagctgccc agctttggag tgtctgggat caatgaatcg 1560
gctgacatga gcattggggt tacagtaata aagaacaata tgataaataa tgaccttgga 1620
ccagcaacag cccagatggc tcttcagcta ttcatcaagg attatcgata cacgtaccga 1680
tgccacaggg gtgatacgca aattcaaaca aggagatcat ttgagctgaa gaagctgtgg 1740
gagcagaccc gttcgaaggc aggattgttg gtctcagatg gagggccaaa tctatacaac 1800
```

```
atccggaatc tccacattcc agaggtctgc ttgaaatggg aattaatgga tgaggattat   1860
cagggcaggc tgtgcaatcc tctgaatccg tttgtcagtc ataaggagat tgagtcggta   1920
aacaatgccg tagtaatgcc agcccatggt ccagcaaaga gcatggaata tgatgccgtt   1980
gcaactacac actcatggat tcctaagagg aaccgttcca ttctcaatac agccaaagg    2040 ggaattcttg aggatgaaca gatgtatcag aagtgctgca atctatttga gaaattcttc   2100
cctagtagtt catataggag gccagttgga atctctagca tggtggaggc catggtgtcc   2160
agggcccgaa ttgacgcacg aattgacttc gagtctggaa ggattaagaa agaagagttt   2220
gccgagatca cgaagatctg ttccaccatt gaagagctca gacggcaaaa atag         2274
```

<210> SEQ ID NO 3
<211> LENGTH: 2151
<212> TYPE: DNA
<213> ORGANISM: Artificial Sequence
<220> FEATURE:
<223> OTHER INFORMATION: Synthesized PA gene nucleotide sequence

<400> SEQUENCE: 3

```
atggaagact ttgtgcgaca atgcttcaat ccaatgatcg tcgagcttgc ggaaaaggca     60
atgaaagagt atggggaaga tccgaaaatc gaaacgaaca agtttgcggc aatatgcacc    120
catttggaag tctgcttcat gtattcagat ttccatttca ttgacgaaag aggcgaatca    180
ataattgtgg aatttggtga tccaaatgta ctattgaaac accgatttga aataattgaa    240
ggaagagacc ggacaatggc atggacagta gtgaatagca tctgtaacac cacaggagtc    300
gaaaaaccta aataccttcc agatctgtat gattacaagg ataaccgatt cattgagatt    360
ggagtgacac ggagggaagt tcacatatac tatctagaaa aggccaacaa gatgaaatcc    420
gagagaacac atattcacat cttctcattt acaggagaag aaatggccac caaagcggat    480
tatacccttg atgaagagag cagggcaagg atcaaaacta gactgttcac cataagacag    540
gaactggcta gcaggggtct atgggattcc tttcgccagt ctgagagagg cgaagagaca    600
attgaagaaa gatttgaaat cacaggaaca atgcgcaggc ttgccgacca aagtctccca    660
ccgaatttct ccagccttga aaactttaga gcctatgtgg atggattcga accgaacggc    720
tgcattgagg gcaagctttc tcagatgtca aaagaagtga ctgccagaat tgagcccttt    780
cttaagacaa caccacgtcc tctcagattg ccggatggac ctccctgttc ccaaaggtca    840
aaattcttac tgatggatgc tttgaaatta agcattgagg acccgagtca tgagggagag    900
gggataccgc tgtatgatgc gatcaaatgc atgaaaacat tttcggctg gaaagagccc    960 aaaattatca aatcacatga gaagggtata aacccaaatt atctcctagc ttggaagcag   1020
gtgctggcag agctccagga cattgaaaat gaggaaaaga tcccaaaaac gaagaacatg   1080
aagaaaacaa gccaattaaa gtgggcatta ggtgagaaca tggcaccaga aaaagtggac   1140
tttgaggatt gcaaagatgt tagtgacctg aaacaatatg acagtgatga gccggagccc   1200
aaatcgctag caagttggat ccaaagtgaa tttaacaaag catgtgagct gaccgattca   1260
agctgggtag aacttgatga aatagggggaa gatgttgccc caatcgagca cattgcgagt   1320
atgagaagga attacttcac agcagaagtg tcgcactgcc gggctaccga gtatataatg   1380
aagggagtgt acataaatac agcattgctc aatgcatctt gtgcagccat ggatgacttc   1440
caattgattc caatgataag caaatgcaga acaaaagaag ggagacggaa aacaaacctg   1500
tatgggttca ttatcaaggg aaggtcccat ttgaggaatg atactgatgt ggtaaacttt   1560
gtgagcatgg aatttttctct tacagacccg aggcttgaac cacacaaatg ggaaaagtac   1620
```

| | |
|---|---|
| tgtgttattg aagtaggga catgctcctg agaacttcaa taggccaggt gtcaaggccc | 1680 |
| atgttcctat acgtgagaac caatggaacc tcaaaaatta aaatgaaatg gggaatggag | 1740 |
| atgaggcgtt gcctccttca atctcttcaa caaattgaga gcatgattga ggcagagtct | 1800 |
| tctatcaaag agaaagacat gaccaaagaa ttttttgaaa acaagtcgga gatgtggccg | 1860 |
| attggagagt cacctaaggg agtggaggaa ggctccatcg ggaaggtgtg caggacatta | 1920 |
| ctagcaaaat ctgtattcaa cagcttgtat gcatctccac agctcgaggg gttttcagct | 1980 |
| gaatcaagaa aattgttact tattgttcag gcacttaggg acaacctgga acctggaacc | 2040 |
| ttcgacattg aaggactata tgaagcaatt gaggagtgcc tgattaatga tccctgggtt | 2100 |
| ttgcttaatg catcttggtt caactccttc ctcacacatg cactgaaata g | 2151 |

<210> SEQ ID NO 4
<211> LENGTH: 1695
<212> TYPE: DNA
<213> ORGANISM: Artificial Sequence
<220> FEATURE:
<223> OTHER INFORMATION: Synthesized HA gene nucleotide sequence

<400> SEQUENCE: 4

| | |
|---|---|
| atggagaaaa tagtgcttct tcttgcaata gtcagtcttg tcaaaagtga tcatatttgc | 60 |
| attggttacc atgcaaacaa ctcgacagag caggttgaca caataatgga aaagaacatt | 120 |
| actgttacac atgcccaaga catactggaa agacacacaa tgggaagct ctgcgatcta | 180 |
| aatggagtga aacctctcat tttaagagat tgtagtgtag ctgggtggct cctcggaaac | 240 |
| ccaatgtgtg acgaattcat caatgtgccg gaatggtctt acatagtgga aaggccaat | 300 |
| ccagccaatg acctctgtta cccagggaat ttcaacgact atgaagaact gaaacaccta | 360 |
| ttgagcagaa taaaccattt tgagaaaata cagatcatcc ccaaaagttc ttggtccgat | 420 |
| catgaagcct cattagggt gagctcagca tgtccatacc agggaagttc ctcctttttc | 480 |
| agaaatgtgg tatggcttat caaaaagaac aatacatacc caacaataaa gagaagctac | 540 |
| aataatacca ccaagaaga tctcttggta ctgtggggga ttcaccatcc taatgatgag | 600 |
| gcagagcaga caaggctcta tcaaaatcca accacctata tttccgttgg gacatcaaca | 660 |
| ctaaaccaga gattggtacc aaaaatagct actagatcca agtaaacgg caaagtgga | 720 |
| aggatggatt tcttttggac aattttaaaa ccgaatgatg caattaactt cgagagtaat | 780 |
| ggaaatttca ttgctccaga atatgcatac aaaattatca gaaaggga ctcagcaatt | 840 |
| atgaaaagtg aattggaata tggtaactgc aacaccaagt gtcaaactcc aatggggggcg | 900 |
| ataaactcta gtatgccgtt ccacaacata caccccctca ccatcgggga atgccccaaa | 960 |
| tatgtgaaat caaacagatt agtccttgcg actggactca gaaataccc tcaaagagag | 1020 |
| agcagaggac tatttggagc catagcaggt tttatagagg aggatggca gggaatggta | 1080 |
| gatggttggt atgggtacca ccatagcaat gagcagggga gtggatacgc tgcagacaaa | 1140 |
| gaatccactc aaaaggcaat agatggagtc accaataagg tcaactcgat cattgacaaa | 1200 |
| atgaacactc aatttgaggc cgttggaaag gaatttaata acttggaaag gaggatagag | 1260 |
| aatttacata gcagatgga agacggattc ctagatgtct ggacttataa tgctgaactt | 1320 |
| ctggttctca tggaaaatga gagaactcta gactttcatg actcaaatgt caagaacctt | 1380 |
| tatgacaagg tccgactaca gcttagggat aatgcaaagg agctgggtaa tggttgtttc | 1440 |
| gagttctatc acaaatgtga taatgaatgt atggaaagtg taaaaaacgg aacgtatgac | 1500 |

| tacccgcagt attcagaaga agcaagacta aacagagagg aaataagtgg agtaaaattg | 1560 |
| gaatcaatgg gaacttacca aatactatca atttattcaa cagtggcgag ttccctagca | 1620 |
| ctggcaatca tggtagctgg tctatcttta tggatgtgct ccaatggatc gttacaatgc | 1680 |
| agaatttgca tttaa | 1695 |

```
<210> SEQ ID NO 5
<211> LENGTH: 1497
<212> TYPE: DNA
<213> ORGANISM: Artificial Sequence
<220> FEATURE:
<223> OTHER INFORMATION: Synthesized NP gene nucleotide sequence

<400> SEQUENCE: 5
```

| atggcgcttc aaggcaccaa acgatcttat gagcagatgg aaactggtgg agaacgccag | 60 |
| aatgctactg agatcagagc atctgttggg agaatggttg gtggaatcgg aagattctac | 120 |
| atacagatgt gcactgaact caaactcagc gaccacgaag gcaggctgat ccaaaacagc | 180 |
| ataacaatag agagaatggt cctctctgca tttgatgaga ggaggaacag gtacctggaa | 240 |
| gaaaatccca gtgcggggaa ggatccgaag aaaactggag gtccaatcta caaaagaagg | 300 |
| gaaggaaagt gggtgagaga gctgattctg tatgacaaag aggagatcag agaatctgg | 360 |
| cgtcaagcga acaatggaga agacgcaact gctggtctca cccatctgat gatctggcat | 420 |
| tccaatctga atgatgccac atatcaaaga acaagagctc ttgtgcgcac tgggatggac | 480 |
| cccagaatgt gttctctgat gcaaggatca actctcccga agatcagg agctgctggt | 540 |
| gcagcagtaa agggaattgg acaatggtg atggaactaa ttcggatgat aaagcgagga | 600 |
| atcaatgacc ggaatttctg gagaggcgac aatggacgaa gaacaaggat tgcatatgag | 660 |
| agaatgtgca acatcctcaa agggaaattc caaacagcag cacaacgagc aatgatggac | 720 |
| caagtgcggg aaagcagaaa tcctgggaat gctgaaattg aagacctta ctttctggca | 780 |
| cggtctgcac tcattctgag aggatcagtg gcccataagt cctgtttgcc tgcttgtgtc | 840 |
| tatgggcttg ctgtagccag tggatatgac tttgagagag aagggtactc tctggtcgga | 900 |
| atagatcctt tcgtctgct ccaaaacagc caggtgttca gcctcattag atcaaatgag | 960 |
| aacccagcac ataaaagtca actggtatgg atggcatgtc attctgcagc atttgaagac | 1020 |
| ctgagagtgt caagcttcat cagaggaaca agagtaatcc aaggggaca actgtccacc | 1080 |
| agaggtgttc aaatagcttc aaatgagaac atggaaacaa tagactccag cactcttgaa | 1140 |
| ctaagaagca gatactgggc tataaggacc aggagtggag aaacaccaa ccaacataga | 1200 |
| gcatctgcag ggcaaatcag tgtacaacct actttctcgg tacagagaag ccttcctttc | 1260 |
| gagagagcaa ccatcatggc ggcattcaca gggaacactg aaggcagaac atccgacatg | 1320 |
| aggactgaaa tcataagaat gatggaaaat gccaaaccag aagacgtgtc tttccaaggg | 1380 |
| cggggagtct tcgagctctc ggacgaaaag gcaacgagcc cgatcgtgcc ttcctttgac | 1440 |
| atgagtaatg aaggatctta tttcttcgga gacaatgcag aggagtatga caattaa | 1497 |

```
<210> SEQ ID NO 6
<211> LENGTH: 1401
<212> TYPE: DNA
<213> ORGANISM: Artificial Sequence
<220> FEATURE:
<223> OTHER INFORMATION: Synthesized NA gene nucleotide sequence

<400> SEQUENCE: 6
```

| atgaatccaa atcagaagat aatagcaatt ggctctgttt ctctaactat tgcgacaata | 60 |

| | |
|---|---|
| tgtttcctca tgcagattgc catcttagca acgactatga cactacattt caagcagaat | 120 |
| gaatgcagca acccctcgaa taatcaagta gtgccatgtg aaccaatcat aatagaaagg | 180 |
| aacatagtgc atttgaatag tactaccata gagaaggaaa tttgtcctaa agtgacagaa | 240 |
| tacaagaatt ggtcaaaacc acaatgtcaa attacagggt tcgctccttt ctccaaggac | 300 |
| aactcaatta ggcttttccgc aggtggggat atctgggtga caagagaacc ttatgtgtcg | 360 |
| tgcggtcttg gtaaatgtta tcaatttgca cttgggcagg gaaccacttt gaaaacaaa | 420 |
| cactcaaatg gcactacacg tgatagaatt cctcatagaa ccctttttaat gaatgagttg | 480 |
| ggtgtcccgt ttcatttggg aaccaaacaa gtgtgcatag catggtccag ctcaagctgc | 540 |
| catgatggga aagcatggtt acatgtttgt gtcactgggg atgataaaaa tgcgactgct | 600 |
| agtatcattt atgatgggat gcttgttgac agtattggtt catggtctaa aaacatcctc | 660 |
| agaactcagg agtcagaatg cgtttgcatc aatggaactt gtacagtagt aatgactgat | 720 |
| ggaagtgcat caggaaaggc tgacactaga atactattca taagagaggg gaaaattgtt | 780 |
| cacattagcc cattgtcagg aagtgctcag catgtggagg aatgctcctg ttaccccgg | 840 |
| tatccagaag ttaggtgtgt ttgcagagac aattggaagg gctccaatag gcccgttcta | 900 |
| tatataaata tggcagatta tagtattaag tccagttatg tgtgctcagg acttgttggc | 960 |
| gacacaccaa gaaatgatga taactccagc agcagcaact gcagggatcc taataacgag | 1020 |
| agaggggccc caggagtgaa agggtgggcc tttgacaatg gaaatgatat ttggatggga | 1080 |
| cgaacaatca agaggatttt acgctcaggt tatgagactt tcagggtcgt tggtggttgg | 1140 |
| accacggcta attccaagtc acagataaat agacaagtca tagttgacag tgacaactgg | 1200 |
| tctgggtatt ctggtatctt ctctgttgaa ggcaaaaact gcatcaacag gtgttttat | 1260 |
| gtggagttga taagaggaag accacaggag actaaggtgt ggtggacttc aaatagcatc | 1320 |
| attgtatttt gtggaacctc aggtacctat ggaacaggct catggcctga tgggcgaat | 1380 |
| atcaacttca tgcctatata a | 1401 |

<210> SEQ ID NO 7
<211> LENGTH: 982
<212> TYPE: DNA
<213> ORGANISM: Artificial Sequence
<220> FEATURE:
<223> OTHER INFORMATION: Synthesized M gene nucleotide sequence

<400> SEQUENCE: 7

| | |
|---|---|
| atgagtcttc taaccgaggt cgaaacgtac gttctctcta tcatcccgtc aggccccctc | 60 |
| aaagccgaga tcgcgcagag acttgaagat gtctttgcag ggaagaacac agatcttgag | 120 |
| gctctcatgg aatggctaaa gacaagacca atcctgtcac ctctgactaa ggggatttta | 180 |
| gggtttgtgt tcacgctcac cgtgcccagt gagcgaggac tgcagcgtag acgatttgtc | 240 |
| caaaatgccc taaatgggaa tggagaccca acaacatgg acaggcagt caaactatac | 300 |
| aagaagctga gagggagat gacattccat ggagcaaagg aagttgcact cagttattca | 360 |
| actggtgcgc ttgccagttg catgggtctc atatacaacc ggatgggaac ggtaacaaca | 420 |
| gaagtggctc ttggcctggt atgtgccact tgtgagcaga ttgctgattc acaccatagg | 480 |
| tctcacagac agatggtgac taccaccaac ccactaatca ggcatgagaa cagaatggta | 540 |
| ctagccagca ctacagctaa ggccatggag caaatggctg gctcgagcga gcaggcagcg | 600 |
| gaagccatgg aggttgcaag tcaggctagg cagatggtgc aggcgatgag gacaattggg | 660 |

```
actcaaccta gctccagtgc aggtctgaaa gatgatctta ttgaaaattt gcaggcctac    720
cagaaacgga tgggagtgca gatgcagcga ttcaagtgat tctctcgttg ttgcagcaag    780
tgtcattggg atattgcact tgatattgtg gattcttgat cgtctttttct tcaaatgcat    840 ttatcgtcgc tttaaatacg gtttgaaaag agggccttct acggaaggag tgcctgagtc    900
tatgagggaa gagtatcggc aggagcagca gagtgctgtg aatgttgacg atggtcattt    960
tgtcaacata gagctggagt aa                                             982
```

<210> SEQ ID NO 8
<211> LENGTH: 838
<212> TYPE: DNA
<213> ORGANISM: Artificial Sequence
<220> FEATURE:
<223> OTHER INFORMATION: Synthesized NS gene nucleotide sequence

<400> SEQUENCE: 8

```
atggattcca acactgtgtc aagcttccag gtagactgct ttctttggca tgtccgcaaa     60
cgatttgcag accaaggacg gggtgatgcc ccatttctag accggcttcg ccagagatcag   120 aagtccctaa gaagaagagg cagcactctt ggtctggaca tcagaaccgc tactcatgaa   180
ggaaagcata tagtggagca gattctggag aagagtcag atgaggcatt taaaatgact   240
attgcttcag tgctagctcc acgctaccta actgacatga ctattgaaga aatgtcaagg   300
gattggttga tgctcattcc caaacagaaa gtgacagggt ctctttgcat tagaatggac   360
caagcaatag tggataaaac catcacactg aaagcaaact tcagtgttac tttcaatcga   420
ctggaagctc taatactact tagagctttt acagatgaag gggcaatagt gggcgaaatc   480
tcaccattac cttctcttcc aggacatact gatgaggatg tcaaaaatgc aattgagatc   540
ctcatcggag gatttgaatg gaatgataac acagttcgag tctctgaaac tctacagaga   600
ttcgcttgga gaagcagcga tgaggatggg agatctccac tctctccaaa gtagaaacgg   660
gaaatggaga gaacaattga gccagaagtt tgaagaaata gatggctga ttgaagaagt   720 gcgacatagg ttaagatta cagagaatag ctttgaacaa ataacattta tgcaagcctt   780
gcaactattg cttgaagtgg agcaagagat aagaactttc tcgtttcagc ttatttaa    838
```

<210> SEQ ID NO 9
<211> LENGTH: 1689
<212> TYPE: DNA
<213> ORGANISM: Artificial Sequence
<220> FEATURE:
<223> OTHER INFORMATION: Modified rHA gene nucleotide sequence

<400> SEQUENCE: 9
atggagaaaa tagtacttct tctttcagtg gttggccttg ttaaaagtga tcagatttgc 60
attggttacc atgcaaacaa ctcgacagag caggttgaca caataatgga aaaaaacgtc 120
actgttacgc atgcccaaga catactggaa aagacacaca acgggaagct ctgcaatctg 180
aatggagtaa aacctctgat ttaaaagaat tgtagtgtag ctggatggct tcttggaaac 240
ccaatgtgcg acgagttcat tagcgtgccg gaatggtctt atatagtgga gagggctaac 300
ccagccaatg acctctgtta cccagggaac ctcaatgact atgaagaact gaaacaccta 360
ttaagcagaa taaatcattt tgagaagact cagatcatcc ccaagaggtc ttggtccaat 420
catacatcat caggagtgag cgcagcatgt ccataccaag gagtggcctc ctttttaga 480 aatgtagtat ggcttaccaa aaagaatgat gcatacccga caataaagat gagctacaat 540
aataccaata aagaagacct tttgatactg tggggaattc atcattccaa cagtgcagag 600

```
gagcagacag atctctacaa gaatccaacc acctatgttt ccgttggaac atcaacacta    660
aaccagaggt tggtgccaaa aatagctacc agatcccaag taaatgggca acgtggaaga    720
atggatttct tctggacaat tttaagaccg aatgatgcaa tccacttcga gagtaatgga    780
aattttatcg ctccagaata tgcatacaaa attatcaaga cgggagactc accaattatg    840
aaaagtgaaa tagaatatgg cgactgcaac accaagtgtc aaactccaat aggggcgata    900
aactctagta tgccattccc caatatacat catctcacta tcggggagtg ccccaaatat    960
gtgaaatcac acaagttagt ccttgcgact gggctcagaa atagtcctct aagagaaaga   1020
ggactgtttg gagctatagc aggatttata gagggaggat ggcaaggaat ggtagatggt   1080
tggtatgggt accatcatag taatgaacag gggagtgggt acgctgcaga cagagaatcc   1140
acccaaaagg caatagatgg agtcaccaac aaggtcaact cgataattga caaaatgaac   1200
actcaatttg aggcagttgg aagagaattt aacagcttag aacggagaat agagaattta   1260
aataagaaaa tggaagacgg attcctagat gtctggactt ataatgctga acttttagtt   1320
ctcatggaaa atgagagaac tctagatttc catgactcaa atgtcaagaa cctttatgac   1380
aaagtccgac tacagcttag ggataatgca aaggagctgg gtaatggttg tttcgagttc   1440
tatcacaaat gtgataatga atgtatggaa agtgtaagaa atggaacgta tgactacccc   1500
cagtactcag aggaagcaag attaaaaagg gaagaaataa gcggagtgaa attggaatca   1560
ataggaactt tccaaatact gtcaatttat tcaacagtgg cgagttccct agtactggca   1620
atcattgtgg ctggtctatc tttatggatg tgctccaatg ggtcgttaca atgcagaatt   1680
tgcatttaa                                                           1689

<210> SEQ ID NO 10
<211> LENGTH: 17
<212> TYPE: DNA
<213> ORGANISM: Artificial Sequence
<220> FEATURE:
<223> OTHER INFORMATION: Primer pCI-EarI-1

<400> SEQUENCE: 10
tagcgagagg ccgcacg                                                    17

<210> SEQ ID NO 11
<211> LENGTH: 27
<212> TYPE: DNA
<213> ORGANISM: Artificial Sequence
<220> FEATURE:
<223> OTHER INFORMATION: Primer pCI-EarI-2

<400> SEQUENCE: 11
tcttcgttcg gtcacagctt ctgtaag                                         27

<210> SEQ ID NO 12
<211> LENGTH: 35
<212> TYPE: DNA
<213> ORGANISM: Artificial Sequence
<220> FEATURE:
<223> OTHER INFORMATION: Terminator sequence

<400> SEQUENCE: 12
ccagggtact ggtcctgacc acgttggagg gggga                                35

<210> SEQ ID NO 13
<211> LENGTH: 42
<212> TYPE: DNA
```

```
<213> ORGANISM: Artificial Sequence
<220> FEATURE:
<223> OTHER INFORMATION: Primer GD123-HA1-F

<400> SEQUENCE: 13
ctcagaaata gtcctctaag agaaagagga ctgtttggag ct         42

<210> SEQ ID NO 14
<211> LENGTH: 38
<212> TYPE: DNA
<213> ORGANISM: Artificial Sequence
<220> FEATURE:
<223> OTHER INFORMATION: Primer GD123-HA2-R

<400> SEQUENCE: 14
aaacagtcct ctttctctta gaggactatt tctgagcc              38

<210> SEQ ID NO 15
<211> LENGTH: 12
<212> TYPE: PRT
<213> ORGANISM: Artificial Sequence
<220> FEATURE:
<223> OTHER INFORMATION: GD123-HA cleavage site amino acid sequence

<400> SEQUENCE: 15

Pro Leu Arg Glu Arg Arg Arg Lys Arg Gly Leu Phe
1               5                   10

<210> SEQ ID NO 16
<211> LENGTH: 36
<212> TYPE: DNA
<213> ORGANISM: Artificial Sequence
<220> FEATURE:
<223> OTHER INFORMATION: GD123-HA cleavage site nucleotide sequence

<400> SEQUENCE: 16
cctctaagag aaagaagaag gaaagagga ctgttt                 36

<210> SEQ ID NO 17
<211> LENGTH: 8
<212> TYPE: PRT
<213> ORGANISM: Artificial Sequence
<220> FEATURE:
<223> OTHER INFORMATION: GD123-rHA cleavage site amino acid sequence

<400> SEQUENCE: 17

Pro Leu Arg Glu Arg Gly Leu Phe
1               5

<210> SEQ ID NO 18
<211> LENGTH: 24
<212> TYPE: DNA
<213> ORGANISM: Artificial Sequence
<220> FEATURE:
<223> OTHER INFORMATION: GD123-rHA cleavage site nucleotide sequence

<400> SEQUENCE: 18
cctctaagag aaagaggact gttt                             24
```